United States Patent
Shinojima et al.

[11] Patent Number: 5,700,784
[45] Date of Patent: Dec. 23, 1997

[54] EXTERNAL PREPARATION FOR SKIN

[75] Inventors: Satoshi Shinojima; Masaru Suetsugu; Yoshihiro Morikawa; Yuki Shibata; Rumiko Kaku, all of Yokohama, Japan

[73] Assignee: Shiseido Co., Ltd., Tokyo, Japan

[21] Appl. No.: 328,066

[22] Filed: Oct. 24, 1994

[30] Foreign Application Priority Data

Oct. 26, 1993 [JP] Japan ................. 5-289951

[51] Int. Cl.$^6$ ............. A61K 31/70; A61K 31/60; A61K 31/62
[52] U.S. Cl. ............. 514/24; 514/25; 514/159; 514/161
[58] Field of Search ............. 514/24, 25, 159, 514/161

[56] References Cited

U.S. PATENT DOCUMENTS 3,279,990   10/1966   Rose et al. ................. 514/25

FOREIGN PATENT DOCUMENTS

| A0398484 | 11/1990 | European Pat. Off. . |
| A0526302 | 3/1993 | European Pat. Off. . |
| A2577805 | 8/1996 | France . |
| 6065051 | 3/1994 | Japan . |

OTHER PUBLICATIONS

Chemical Abstracts, vol. 105, No. 14 issued 14 Oct. 1986, Wagner et al., "Analyses and standardization of pharmaceuticals and plant preparations by HPLC and other chromatographic methods. 6. *Primula* root extract. HPLC analysis", see p. 380, column 2, abstract no. 120873v, Dtsch. Apoth. Ztg., 126(28), 1489–1493.

Chemical Abstracts (116: 18 09 90 ) Studies on the Chemical Constituents of Glorisa Rothschidiana and Colchicum autumnel mimaki et al. (1991).

Chemical Abstracts (121:91340) Skin–lightening preparations containing gentistic acid ester glycosidis Shinojima et al. (1994).

Derwent Publications' Abstract of AN 92–197397 & JP–A–4 131 091.

*Primary Examiner*—Kevin E. Weddington
*Attorney, Agent, or Firm*—Townsend & Banta

[57] ABSTRACT

An external preparation for the skin comprising at least one of the glycosides or hydroxysaliyclic acid and/or the glycosides of aliphatic esters of hydroxysalicylic acid represented by the following formula 1:

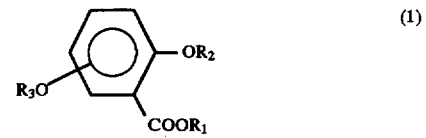

wherein $R_1$ represents one selected from the group consisting of saturated hydrocarbon group and an unsaturated hydrocarbon group which have 1 to 20 carbon atoms and which may be either a straight-chain or a branched chain, and one of $R_2$ and $R_3$ represents a sugar residue and the other hydrogen. The external preparation for the skin has an excellent whitening effect and/or an excellent skin care effect.

3 Claims, No Drawings

EXTERNAL PREPARATION FOR SKIN

FIELD OF THE INVENTION

The present invention relates to an external preparation for skin and, more particularly, to an external preparation for skin having an excellent whitening effect.

BACKGROUND OF THE INVENTION

The mechanism of a chloasma is partially known but it is generally considered that a melanin pigment is produced under abnormality of hormone stimulus of ultraviolet rays from the sun and abnormally settles in. Examples of remedies for such a chloasma or a birthmark are, a method of administration of a large amount of a substance which suppresses the generation of melanin such as vitamin C, a method of injecting glutathione or the like, and a method of applying kojic acid, vitamin C, cystein or the like to the topical part in the form of ointment, cream, lotion or the like. In Europe and the U.S.A., a hydroquinone composition is used.

However, since these compounds except for the hydroquinone composition manifest the effect very slowly, they do not produce an adequate whitening effect. On the other hand, although the effect of hydroquinone is recognized for the present, since it has a sensitization property, use thereof is generally limited.

In order to improve the safety of hydroquinone, an attempt has recently been made at forming hydroquinone into an alkyl monoether of higher alcohols, but no product which is sufficiently safe has been produced.

SUMMARY OF THE INVENTION

Accordingly, it is an object of the present invention to eliminate the above-described problems in the related art and to provide a safe whitening agent having excellent whitening effect, and an external preparation for skin containing such a whitening agent.

As a result of studies undertaken by the present inventors so as to achieve this aim, it has been found that a specific glycoside among the glycosides of hydroxysalicylic acid and the glycosides of aliphatic esters of hydroxysalicylic acid has a stronger whitening effect than hydroquinone, and that it is possible to produce a safe external preparation for skin having excellent whitening effect from such a specific glycoside.

The present invention provides an external preparation for skin comprising at least one of the glycosides of hydroxysalicylic acid and/or the glycosides of aliphatic esters of hydroxysalicylic acid represented by the formula 1:

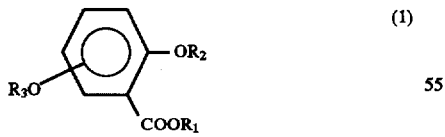

(1)

wherein $R_1$ represents one selected from the group consisting of a saturated hydrocarbon group and an unsaturated hydrocarbon group which have 1 to 20 carbon atoms and which may be a straight-chain or a branched-chain, and one of $R_2$ and $R_3$ represents a sugar residue and the other hydrogen.

A glycoside of hydroxysalicylic acid or a glycoside of a hydroxysalicylate is a substance represented by the formula 1 wherein $R_1$ represents one selected from the group consisting of a saturated hydrocarbon group and an unsaturated hydrocarbon group which have 1 to 20 carbon atoms and which may be a straight-chain or a branched-chain. The branched-chain unsaturated hydrocarbon group contains an aromatic hydrocarbon group such as a phenyl group and a benzyl group.

One of $R_2$ and $R_3$ in the formula 1 represents a sugar residue and the other hydrogen. Examples of the sugar residue are pentose residue, hexose residue, amino sugar residue and uronic acid residue.

The compound of the present invention, i.e., a glycoside of hydroxysalicylic acid or a glycoside of a hydroxysalicylate can be obtained by reacting hydroxysalicylic acid or a hydroxysalicylate with an acetylated glucose such as pentaacetyl glucose (or an acetobromoglucose) in the presence of an acid catalyst, It is also possible to obtain the compound of the present invention by the condensation of a hydroxysalicylate with pentaacetyl glucose by the known synthesis (Arch Pharm., 291 (1958)).

Examples of the compound are shown in the following.

3-β-D-Glucopyranosylocysalicylic acid
Methyl 3-β-D-glucopyranosyloxysalicylate
Ethyl 3-β-D-glucopyranosyloxysalicylate
Propyl 3-β-D-glucopyranosyloxysalicylate
Isopropyl 3-β-D-glucopyranosyloxysalicylate
4-β-D-Glucopyranosylocysalicylic acid
Methyl 4-β-D-glucopyranosyloxysalicylate
Ethyl 4-β-D-glucopyranosyloxysalicylate
Propyl 4-β-D-glucopyranosyloxysalicylate
Isopropyl 4-β-D-glucopyranosyloxysalicylate
5-β-D-Glucopyranosylocysalicylic acid
Methyl 5-β-D-glucopyranosyloxysalicylate
Ethyl 5-β-D-glucopyranosyloxysalicylate
Propyl 5-β-D-glucopyranosyloxysalicylate
Isopropyl 5-β-D-glucopyranosyloxysalicylate
6-β-D-Glucopyranosylocysalicylic acid
Methyl 6-β-D-glucopyranosyloxysalicylate
Ethyl 6-β-D-glucopyranosyloxysalicylate
Propyl 6-β-D-glucopyranosyloxysalicylate
Isopropyl 6-β-D-glucopyranosyloxysalicylate
2-β-D-Glucopyranosyloxysalicylic-3-hydroxybenzoic acid
Methyl 2-β-D-glucopyranosyloxysalicylic-3-hydroxybenzoate
Ethyl 2-β-D-glucopyranosyloxysalicylic-3-hydroxybenzoate
Propyl 2-β-D-glucopyranosyloxysalicylic-3-hydroxybenzoate
Isopropyl 2-β-D-glucopyranosyloxysalicylic-3-hydroxybenzoate
2-β-D-Glucopyranosyloxysalicylic-4-hydroxybenzoic acid
Methyl 2-β-D-glucopyranosyloxysalicylic-4-hydroxybenzoate
Ethyl 2-β-D-glucopyranosyloxysalicylic-4-hydroxybenzoate
Propyl 2-β-D-glucopyranosyloxysalicylic-4-hydroxybenzoate
Isopropyl 2-β-D-glucopyranosyloxysalicylic-4-hydroxybenzoate
2-β-D-Glucopyranosyloxysalicylic-5-hydroxybenzoic acid Methyl 2-5-β-D-glucopyranosyloxysalicylic-5-hydroxybenzoate Ethyl 2-5-β-D-glucopyranosyloxysalicylic-5-hydroxybenzoate Propyl 2-5-β-D-glucopyranosyloxysalicylic-5-hydroxybenzoate Isopropyl 2-β-D-glucopyranosyloxysalicylic-5-hydroxybenzoate Among these compounds, straight-chain or branched-chain esters having 1 to 8 carbon atoms, especially, 1 to 6 carbon atoms are preferable from the point of view of whitening effect and irritation.

It has also been found that among the glycosides of a hydroxysalicylate of the present invention, 2-β-D-Glucopyranosyloxy-5-hydroxybenzoates (hereinunder referred to as "glycosides of gentisate") represented by the following formula 2 have a skin care effect as well as a whitening effect.

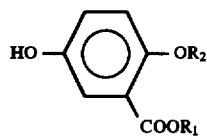

(2)

wherein $R_1$ represents one selected from the group consisting of a saturated hydrocarbon group and an unsaturated hydrocarbon group which have 1 to 20 carbon atoms and which may be of either a straight-chain or a branched-chain, and $R_2$ represents one selected from the group consisting of pentose residue hexose residue, amino sugar residue and uronic acid residue.

Examples of such a glycoside of gentisate other than the above-described 2-β-D-Glucopyranosyloxy-5-hydroxybenzoate are as follows:

Butyl 2-β-D-glucopyranosyloxy-5-hydroxybenzoate

2-Methyl-1-propyl 2-β-D-glucopyranosyloxy-5-hydroxybenzoate

2-Methyl-2-propyl 2-β-D-glucopyranosyloxy-5-hydroxybenzoate

Pentyl 2-β-D-glucopyranosyloxy-5-hydroxybenzoate

2-Pentyl 2-β-D-glucopyranosyloxy-5-hydroxybenzoate

3-Pentyl 2-β-D-glucopyranosyloxy-5-hydroxybenzoate tert-Amyl 2-β-D-glucopyranosyloxy-5-hydroxybenzoate 2-Methyl-1-butyl 2-β-D-glucopyranosyloxy-5-hydroxybenzoate 2-Methyl-2-butyl 2-β-D-glucopyranosyloxy-5-hydroxbenzoate Neopentyl 2-β-D-glucopyranosyloxy-5-hydroxybenzoate Hexyl 2-β-D-glucopyranosyloxy-5-hydroxybenzoate 2-βMethyl-1-pentyl 2-β-D-glucopyranosyloxy-5-hydroxybenzoate 2-Methyl-2-pentyl 2-β-D-glucopyranosyloxy-5-hydroxybenzoate 2-Methyl-3-pentyl 2-β-D-glucopyranosyloxy-5-hydroxybenzoate 3-Methyl-1-pentyl 2-β-D-glucopyranosyloxy-5-hydroxybenzoate 3-Methyl-2-pentyl 2-β-D-glucopyranosyloxy-5-hydroxybenzoate 3-Methyl-3-pentyl 2-β-D-glucopyranosyloxy-5-hydroxybenzoate 4-Methyl-1-pentyl 2-β-D-glucopyranosyloxy-5-hydroxybenzoate 4-Methyl-2-pentyl 2-β-D-glucopyranosyloxy-5-hydroxybenzoate Heptyl 2-β-D-glucopyranosyloxy-5-hydroxybenzoate 2-Heptyl 2-β-D-glucopyranosyloxy-5-hydroxybenzoate 3-Heptyl 2-β-D-glucogyranosyloxy-5-hydroxybenzoate 2,2-Dimethyl-3-pentyl 2-β-D-glucopyranosyloxy-5-hydroxybenzoate 2,3-Dimethyl-3-pentyl 2-β-D-glucopyranosyloxy-5-hydroxybenzoate 2,4-Dimethyl-3-pentyl 2-β-D-glucopyranosyloxy-5-hydroxybenzoate 4,4-Dimethyl-3-pentyl 2-β-D-glucopyranosyloxy-5-hydroxybenzoate 3-Ethyl-3-pentyl 2-β-D-glucopyranosyloxy-5-hydroxybenzoate 3-Methyl-3-hexyl 2-β-D-glucopyranosyloxy-5-hydroxybenzoate 5-Methyl-2-hexyl 2-β-D-glucopyranosyloxy-5-hydroxybenzoate 2-Tetradecyl 2-β-D-glucopyranosyloxy-5-hydroxybenzoate Pentadecyl 2-β-D-glucopyranosyloxy-5-hydroxybenzoate Hexadecyl 2-β-D-glucopyranosyloxy-5-hydroxybenzoate 2-Hexadecyl 2-β-D-glucopyranosyloxy-5-hydroxybenzoate Heptadecyl 2-β-D-gGlucopyranosyloxy-5-hydroxybenzoate Octadecyl 2-β-D-glucopyranosyloxy-5-hydroxybenzoate Nonadecyl 2-β-D-glucopyranosyloxy-5-hydroxybenzoate Eicodecyl 2-β-D-glucopyranosyloxy-5-hydroxybenzoate Benzyl 2-β-D-glucopyranosyloxy-5-hydroxybenzoate Among these compounds, straight-chain or branched-chain esters having 1 to 8 carbon atoms, especially, 1 to 6 carbon atoms are preferable from the point of view of whitening effect and skin care effect.

The amount of glycoside of hydroxysalicylic acid or a hydroxysalicylate of the present invention added to an external preparation for skin is 0.001 to 20 wt %, preferably 0.01 to 10 wt % of the total amount of external preparation for the skin. If the amount of glycoside is less than 0.001 wt %, the whitening effect is poor, while use of more than 20 wt % of glycoside does not increase the effect.

When vitamin C or a derivative thereof or vitamin E or a derivative thereof is mixed with at least one of the glycosides of hydroxysalicylic acid and the glycosides of a hydroxysalicylate, the whitening effect is increased in comparison with a single use of a glycoside of hydroxysalicylic acid or a glycoside of a hydroxysalicylate. This is considered to be because vitamin C or vitamin E increases the absorbing power of the compound to the skin.

The vitamin C used in the present invention means L-ascorbic acid, which has faculties of cell respiration activation, enzyme activation and collagen formation owing to its strong reducing effect and also has a melanin reducing function. As examples of a derivative of vitamin C will be cited monoalkyl esters of L-ascorbic acid such as L-ascorbic acid monostearate, L-ascorbic acid monopalmitate and L-ascorbic acid monooleate; monoester derivatives of L-ascorbic acid such as magnesium L-ascorbic acid monophosphate and L-ascorbic acid-2-sodium sulfate; dialkyl esters of L-ascorbic acid such as L-ascorbic acid-2, 6-dipalmitate and L-ascorbic acid-2, 6-dioleate; diester derivatives of L- ascorbic acid such as L-ascorbic acid diphosphate; trialkyl esters of L-ascorbic acid such as L-ascorbic acid tristearate, L-ascorbic acid tripalmitate and L-ascorbic acid trioleate; and triester derivatives of L-ascorbic acid such as L-ascorbic acid triphosphate. Among these, at least one L-ascorbic acid derivative is appropriately selected and mixed in the present invention.

As examples of the vitamin E or a derivative thereof used in the present invention will be cited α-tocopherol, β-tocopherol, γ-tocopherol, δ-tocopherol, tocopherol acetate mad tocopherol nicotinate. Among these, at least one is appropriately selected and mixed. The vitamin E may be either natural or synthetic. When natural vitamin E (d-α-tocopherol) is used, it may be either crude or refined.

The amount of vitamin C mixed with an external preparation for the skin of the present invention is 0.0001 to 10 wt %, preferably 0.001 to 3 wt % of the total amount of external preparation for the skin. The amount of vitamin E mixed with an external preparation for the skin of the present invention is 0.0001 to 5 wt % preferably 0.001 to 1 wt % of the total amount of external preparation for the skin.

It is possible to appropriately add an ingredient, as occasion demands, which is used for external preparation for the skin such as general cosmetics and pharmaceuticals, as well as the above-described essential ingredients. Examples of such an ingredient are oil, ultraviolet absorber, antioxidant, surfactant, humectant, perfume, water, alcohol, thickening agent, coloring agent and skin nutrient (e.g., pantothenyl-ethyl ether and glycyrrhetinate).

The ultraviolet absorber are usable benzoic acid ultraviolet absorbers such as para-aminobenzoic acid (hereinunder referred to as "PABA"), glyceryl PABA and ethylhydroxypropyl PABA; cinnamic acid ultraviolet absorbers such as octylmethoxy cinnamate and 2-methyl-p-methoxy cinnamate; benzophenone ultraviolet absorbers such as 2,4-dihydroxybenzophenone and 2-hydroxy-4-methoxy-4'-methyl-benzophenone; and other ultraviolet absorbers such as ethyl urocanate, 2-phenyl-5-methylbenzoxazole, and 4-methoxy-4'-t-butyldibenzoylmethane.

EMBODIMENTS

The present invention will be explained in more detail with reference to the following examples. It is to be understood, however, that the present invention is not limited to these examples. The unit of the mixing amount is wt % unless specified otherwise.

EXAMPLES 1 TO 6, COMPARATIVE EXAMPLES 1 AND 2

A lotion was prepared in accordance with the following prescription and the whitening effect thereof was examined.

(Alcohol phase)

| | |
|---|---|
| 95% ethyl alcohol | 55.0 |
| Polyoxyethylene (25 mol) hardened castor oil ether | 2.0 |
| Antioxidant antiseptic | q.s. |
| Perfume | q.s. |
| Whitening agent (shown in Table 1) | 1.0 |

(Water phase)

| | |
|---|---|
| Glycerin | 5.5 |
| Sodium hexametaphosphate | q.s. |

<Process>

After the water phase and the alcohol phase were prepared, they were solubilized.

TABLE 1

| | Compound |
|---|---|
| Comp. 1 | None |
| Comp. 2 | Hydroquinone |
| Ex. 1 | Methyl 5-β-D-glucopyranosyloxysalicylate |
| Ex. 2 | Ethyl 5-β-D-glucopyranosyloxysalicylate |
| Ex. 3 | Butyl 4-β-D-glucopyranosyloxysaiicylate |
| Ex. 4 | Octyl 4-β-D-glucopyranosyloxysalicylate |
| Ex. 5 | Decyl 3-β-D-glucopyranosyloxysalicylate |
| Ex. 6 | Methyl 2-β-D-glucopyranosyloxy-5-hydroxybenzoate |
| Ex. 7 | Methyl 4-β-D-glucopyranosyloxysalicylate |

Method of Testing the Whitening Effect 90 examinees were divided into 9 groups, each consisting of 10 examinees. The skin of the facies medialis brachi of each examinees was exposed to the sunlight in summer for 4 hours (2 hours per day and 2 days in total). 5 days thereafter, the samples of Examples 1 to 7 and Comparative Examples 1 and 2 were applied to the sunburnt skin of 10 examinees in the respective groups.

Evaluation Method

The whitening effect was judged on the basis of the following criteria.

⊚: Not less than 80% of the examinees showed a distinguished effect or a noticeable effect ○: 50 to less than 80% of the examinees showed a distinguished effect or a noticeable effect ▲: 30 to less than 50% of the examinees showed a distinguished effect or a noticeable effect X: Less than 30% of the examinees showed a distinguished effect or a noticeable effect The results based on these criteria are shown in Table 2.

TABLE 2

| | Whitening effect |
|---|---|
| Comp. 1 | X |
| Comp. 2 | ▲ |
| Ex. 1 | ⊚ |
| Ex. 2 | ○ |
| Ex. 3 | ⊚ |
| Ex. 4 | ⊚ |
| Ex. 5 | ○ |
| Ex. 6 | ⊚ |
| Ex. 7 | ⊚ |

As is clear from Table 2, it was recognized that the samples in Examples 1 to 7 prevented the excess melanin pigment from settling in the skin exposed to the sun and thereby preventing the skin from being tanned in comparison with the samples in Comparative Examples 1 and 2.

EXAMPLES 8 TO 13, COMPARATIVE EXAMPLES 1 AND 2

A lotion was prepared by using a glycoside of a gentisate of the present invention shown in Table 3 in the same way as in Examples 1 to 7, and the whitening effect and the skin care effect were examined.

TABLE 3

| | Compound |
|---|---|
| Comp. 1 | None |
| Comp. 2 | Hydroquinone |
| Ex. 8 | Methyl 2-β-D-glucopyranosyloxy-5-hydroxybenzoate |
| Ex. 9 | Ethyl 5-β-D-glucopyranosyloxy-5-hydroxybenzoate |
| Ex. 10 | Butyl 4-β-D-glucopyranosyloxy-5-hydroxybenzoate |
| Ex. 11 | Octyl 2-β-D-glucopyranosyloxy-5-hydroxybenzoate |
| Ex. 12 | Decyl 2-β-D-glucopyranosyloxy-5-hydroxybenzoate |
| Ex. 13 | 2-hexadecyl-2-β-D-glucopyranosyloxy-5-hydroxybenzoate |

Method of Testing the Skin Care Effect

A sample lotion was applied to the faces of 80 examinees who were suffering from chapped skin or burning skin after sunburn. 2 weeks after, the state of the skin of each examinee was visually judged. A sample lotion was also applied to 80 men examinees suffering from razor rash immediately after they had shaved. Evaluation criteria are as follows.

Chapped Skin Ameliorating Effect

Distinguished effect: The symptom disappeared
Noticeable effect: The symptom was alleviated
Slight effect: The symptom was slightly alleviated
No effect: No change was seen in the symptom

Razor Rash Ameliorating Effect

Distinguished effect: The razor rash disappeared
Noticeable effect: The razor rash were greatly ameliorated
Slight effect: The razor rash was slightly ameliorated
No effect: No change was seen in the razor rash

Judgment

⊚: Not less than 80% of the examinees showed a distinguished effect or a noticeable effect
o: 50 to less than 80% the examinees showed a distinguished effect or a noticeable effect
▲: 30 to less than 50% of the examinees showed a distinguished effect or a noticeable effect
X: Less than 30% of the examinees showed a distinguished effect or a noticeable effect The results based on these criteria are shown in Table 4.

TABLE 4

| | Whitening effect | Chapped skin ameliorating effect |
|---|---|---|
| Comp. 1 | X | X |
| Comp. 2 | ▲ | X |
| Ex. 8 | ⊚ | ⊚ |
| Ex. 9 | o | ⊚ |
| Ex. 10 | ⊚ | o |
| Ex. 11 | ⊚ | ▲ |
| Ex. 12 | o | ▲ |
| Ex. 13 | ⊚ | X |

As is clear from Table 4, the lotions in Examples 8 to 13 can prevent the settlement of excess melanin pigment to the skin exposed to the sunlight, thereby preventing the skin from being tanned in comparison with the lotions in Comparative Examples 1 and 2. In addition, the lotions of the present invention have a chapped skin ameliorating effect.

EXAMPLE 14

(Cream)

| | |
|---|---|
| Solid paraffin | 5.0 |
| Beeswax | 10.0 |
| Vaseline | 15.0 |
| Liquid paraffin | 41.0 |
| Glycerin monostearate | 2.0 |
| Polyoxyethylene (20 mol) sorbitan monolaurate | 2.0 |
| Powder soap | 0.1 |
| Borax | 0.1 |
| 2-Pentyl 5-β-D-glucopyranosyloxy-salicylate | 0.05 |
| 3-Methyl-1-butyl 4-β-D-glucopyranosyl-oxysalicylate | 0.05 |
| Perfume | q.s. |
| Sodium hydrogensulfite | 0.03 |
| Ethylparaben | 0.3 |
| Ion-exchanged water | balance |

<Process>

Powder soap and borax were added to ion-exchanged water and the mixture was heated and held at 70° C. (water phase). The other ingredients were dissolved with heat and held at 70° C. (oil phase). The oil phase was gradually added to the water phase under stirring so as to induce reaction. After the end of the reaction, the reaction product was uniformly emulsified by a homomixer and thereafter the emulsion was cooled to 30° C. under adequate stirring.

The cream obtained in Example 14 had an excellent whitening effect.

EXAMPLE 15

(Milky Lotion)

| | |
|---|---|
| Stearic acid | 2.5 |
| Cetyl alcohol | 1.5 |
| Vaseline | 5.0 |
| Liquid paraffin | 10.0 |
| Polyoxyethylene (10 mol) monooleate | 2.0 |
| Polyethylene glycol 1500 | 3.0 |
| Triethanol amine | 1.0 |
| Isopropyl 2-β-D-glucopyranosyloxy-3-hydroxybenzoate | 0.001 |
| Sodium hydrogensulfite | 0.01 |
| Ethylparaben | 0.3 |
| Carboxyvinyl polymer (trade name: Carbopol 941 produced by B.F. Goodrich Chemical Company) | 0.05 |
| Perfume | q.s. |
| Ion-exchanged water | Balance |

<Process>

Carboxyvinyl polymer was dissolved in a small amount of ion-exchanged water (phase A). Polyethylene glycol 1500 and triethanol amine were added to the remaining ion-exchanged water, and the mixture was melted with heat and held at 70° C. (water phase). The other ingredients were melted with heat and held at 70° C. (oil phase). The oil phase was added to the water phase for the purpose of preliminary emulsification. Thereafter, the phase A was added, and the mixture was uniformly emulsified by a homomixer. The emulsion obtained was cooled to 30° C. under adequate stirring.

The milky lotion obtained in Example 15 had an excellent whitening effect.

EXAMPLE 16

(Milky Lotion)

(Oil phase portion)

| | |
|---|---|
| Stearyl alcohol | 1.5 |
| Squalane | 2.0 |
| Vaseline | 2.5 |
| Deodorized liquid lanolin | 1.5 |
| Evening primrose oil | 2.0 |
| Isopropyl myristate | 5.0 |
| Glycerin monooleate | 2.0 |
| Polyoxyethylene (60 mol) hardened castor oil | 2.0 |
| Tocopherol acetate | 0.05 |
| Ethylparaben | 0.2 |
| Butylparaben | 0.1 |
| 6-β-D-Glucopyranosyloxysalicylic acid | 1.0 |
| Para-aminobenzoic acid | 0.1 |
| Perfume | q.s. |

(Water phase portion)

| | |
|---|---|
| Sodium hydrogensulfite | 0.001 |
| Glycerin | 5.0 |
| Sodium hyaluronate | 0.01 |
| Carboxyvinyl polymer (trade name: Carbopol 941, produced by B.F. Goodrich Chemical Company) | 0.02 |
| Potassium hydroxide | 0.2 |
| Ion-exchanged water | Balance |

<Process>

The oil phase portion was dissolved at 70° C. The water phase portion was also dissolved at 70° C. The oil phase portion was mixed with the water phase portion, and after the mixture was emulsified by an emulsifier, it was cooled to 30° C. by a heat exchanger.

The milky lotion obtained in Example 18 had an excellent whitening effect.

EXAMPLE 17

(Milky Lotion)

(Oil phase portion)

| | |
|---|---|
| Stearyl alcohol | 1.5 |
| Squalane | 2.0 |
| Vaseline | 2.5 |
| Deodorized liquid lanolin | 1.5 |
| Evening primrose oil | 2.0 |
| Isopropyl myristate | 5.0 |
| Glycerin monooleate | 2.0 |
| Polyoxyethylene (60 mol) hardened castor oil | 2.0 |
| Tocopherol acetate | 0.05 |
| Ethylparaben | 0.2 |
| Butylparaben | 0.1 |
| Methyl 4-β-D-glucopyranosyloxysalicylate | 1.0 |
| Para-aminobenzoic acid | 0.1 |
| Perfume | q.s. |

(Water phase portion)

| | |
|---|---|
| Sodium hydrogensulfite | 0.001 |
| Glycerin | 5.0 |
| Sodium hyaluronate | 0.01 |
| Carboxyvinyl polymer (trade name: Carbopol 941, produced by B.F. Goodrich Chemical Company) | 0.02 |
| Potassium hydroxide | 0.2 |
| Ion-exchanged water | Balance |

<Process>

The oil phase portion was dissolved at 70° C. The water phase portion was also dissolved at 70° C. The oil phase portion was mixed with the water phase portion, and after the mixture was emulsified by an emulsifier, it was cooled to 30° C. by a heat exchanger.

The milky lotion obtained in Example 17 had an excellent whitening effect, safety and stability.

EXAMPLE 18

(Milky Lotion)

| | |
|---|---|
| Microcrystalline wax | 1.0 |
| Beeswax | 2.0 |
| Lanolin | 20.0 |
| Liquid paraffin | 10.0 |
| Squalane | 5.0 |
| Sorbitan sesquioleate | 4.0 |
| Polyoxyethylene (20 mol) sorbitan monooleate | 1.0 |
| Propylene glycol | 7.0 |
| Isobutyl 4-β-D-glucopyranosyloxysalicylate | 3.0 |
| Ethylparaben | 0.3 |
| Sodium hydrogensulfite | 0.01 |
| Perfume | q.s. |
| Ion-exchanged water | Balance |

<Process>

Propylene glycol was added to the ion-exchanged water, and the mixture was heated to and held at 70° C. (water phase). The other ingredients were mixed, melted with heat and held at 70° C. (oil phase). The water phase was gradually added to the oil phase which was adequately stirred. The mixture was uniformly emulsified by a homomixer. The emulsion obtained was cooled to 30° C. under adequate stirring.

The milky lotion obtained in Example 18 had an excellent whitening effect.

EXAMPLE 19

(Jelly)

| | |
|---|---|
| 95% ethyl alcohol | 10.0 |
| Dipropylene glycol | 15.0 |
| Polyoxyethylene (50 mol) oleyl alcohol ether | 2.0 |
| Carboxyvinyl polymer (trade name: Carbopol 941, produced by B.F. Goodrich Chemical Company) | 1.00 |
| Caustic soda | 0.15 |
| L-arginine | 0.1 |
| Eicosyl 2-β-D-glucopyranosyloxy-3-hydroxybenzoate | 0.05 |
| Methylparaben | 0.2 |
| Ethylenediamine tetraacetate trisodium dihydrate | 0.05 |
| Perfume | q.s. |
| Ion-exchanged water | Balance |

<Process>

Carbopol 941 was uniformly dissolved in ion-exchanged water. Eicosyl 2-β-D-glucopyranosyloxy-3- hydroxybenzoate and polyoxyethylene (50 mol) oleyl alcohol ether were dissolved in 95% ethanol, and the aqueous Carbopol 941 solution was added to the solution. After the other ingredients were added to the mixed solution, the resultant solution was neutralized by caustic soda and L-arginine and thickened.

The jelly obtained in Example 19 had an excellent whitening effect.

EXAMPLE 20

(Toilet Lotion)

(Phase A)

| | |
|---|---|
| Ethanol (95%) | 10.0 |
| Polyoxyethylene (20 mol) octyldodecanol | 1.0 |
| Methylparaben | 0.15 |
| Pantothenyl ethyl ether | 0.1 |
| Hexyl 3-β-D-glucopyranosyloxysalicylate | 0.05 |

(Phase B)

| | |
|---|---|
| Potassium hydroxide | 0.1 |

(Phase C)

| | |
|---|---|
| Glycerin | 5.0 |
| Dipropylene glycol | 10.0 |
| Sodium hydrogensulfite | 0.03 |
| Carboxyvinyl polymer (trade name: Carbopol 941, produced by B.F. Goodrich Chemical Company) | 0.2 |
| Ion-exchanged water | Balance |

<Process>

The phase A and the phase C were uniformly dissolved respectively, and the phase A was added to the phase C so as to be solubilized. The phase B was then added to the mixed solution, and the resultant solution was packed.

The toilet lotion obtained in Example 20 had an excellent whitening effect.

EXAMPLE 21

(Pack Containing Powder)

(Alcohol phase)

| | |
|---|---|
| 95% ethanol | 10.0 |
| Propylene glycol | 5.0 |
| 2-Hexadecyl 6-β-D-glucopyranosyl-oxysalicylate | 10.0 |
| Propyl 4-β-D-glucopyranosyl-oxysalicylate | 1.0 |
| Perfume | q.s. |
| Coloring agent | q.s. |

(Water phase)

| | |
|---|---|
| Zinc white | 25.0 |
| Kaolin | 20.0 |
| Methylparaben | 0.3 |
| Glycerin | 5.0 |
| Ion-exchanged water | Balance |

<Process>

After the water phase was uniformly prepared, the alcohol phase prepared at room temperature was added thereto and the mixture was uniformly mixed.

The pack obtained in Example 21 had an excellent whitening effect.

EXAMPLE 22

(Cream)

| | |
|---|---|
| Solid paraffin | 5.0 |
| Beeswax | 10.0 |
| Vaseline | 15.0 |
| Liquid paraffin | 41.0 |
| Glycerin monostearate | 2.0 |
| Polyoxyethylene (20 mol) sorbitan monolaurate | 2.0 |
| Powder soap | 0.1 |
| Borax | 0.2 |
| Dodecyl 2-β-D-glucopyranosyloxy-5-hydroxybenzoate | 0.05 |
| Sodium hydrogensulfite | 0.03 |
| Ethylparaben | 0.3 |
| Perfume | q.s. |
| Ion-exchanged water | Balance |

<Process>

Powder soap and borax were added to ion-exchanged water and the mixture was heated and held at 70° C. (water phase).

The other ingredients were melted with heat and held at 70° C. (oil phase). The oil phase was gradually added to the water phase under stirring so as to induce reaction. After the end of the reaction, the reaction product was uniformly emulsified by a homomixer and thereafter the emulsion was cooled to 30° C. under adequate stirring.

The cream obtained in Example 22 had an excellent whitening effect and also an excellent chapped skin ameliorating effect.

EXAMPLE 23

(Cream)

| | |
|---|---|
| Stearyl alcohol | 4.0 |
| Stearic acid | 5.0 |
| Isopropyl myristate | 18.0 |
| Glycerin monostearate | 3.0 |
| Propylene glycol | 10.0 |
| Ethyl 2-β-D-glucopyranosyloxy-5-hydroxybenzoate | 20.0 |
| Caustic potassium | 0.2 |
| Sodium hydrogensulfite | 0.01 |
| Antiseptic | q.s. |
| Perfume | q.s. |
| Ion-exchanged water | Balance |

<Process>

Propylene glycol and caustic potassium were added to ion-exchanged water and the mixture was heated and held at 70° C. (water phase). The other ingredients were melted with heat and held at 70° C. (oil phase). The oil phase was gradually added to the water, and the temperature was maintained at the same temperature awhile after the entire amount of oil phase was added so as to induce reaction. After the end of the reaction, the reaction product was uniformly emulsified by a homomixer and thereafter the emulsion was cooled to 30° C. under adequate stirring.

The cream obtained in Example 23 had an excellent whitening effect and an excellent chapped skin ameliorating effect.

EXAMPLE 24

(Cream Containing Vitamin C)

| | |
|---|---|
| Stearic acid | 6.0 |
| Sorbitan monostearate | 2.0 |
| Polyoxyethylene (20 mol) hardened castor oil ether | 1.5 |
| Propylene glycol | 10.0 |
| Isopropyl 2-β-D-glucopyranosyloxy-5-hydroxybenzoate | 5.0 |
| Glycerin octanoate | 10.0 |
| Squalene | 5.0 |
| Vitamin C | 0.1 |
| Sodium hydrogensulfite | 0.001 |
| Ethylparaben | 0.3 |
| Perfume | q.s. |
| Ion-exchanged water | Balance |

<Process>

Propylene glycol and vitamin C were added to ion-exchanged water and the mixture was heated and held at 70° C. (water phase). The other ingredients were melted with heat and held at 70° C. (oil phase). The oil phase was gradually added to the water phase for the purpose of preliminary emulsification, and thereafter, the mixture was uniformly emulsified by a homomixer. The emulsion was cooled to 30° C. under adequate stirring.

The cream obtained in Example 24 had a more excellent whitening effect than a cream which did not contain vitamin C.

EXAMPLE 25

(Cream Containing Vitamin E)

| | |
|---|---|
| Stearyl alcohol | 7.0 |
| Stearic acid | 2.0 |
| Hydrogenated lanolin | 2.0 |
| Squalane | 5.0 |
| 2-Octyldodecyl alcohol | 6.0 |
| Polyoxyethylene (25 mol) cetyl alcohol ether | 3.0 |
| Glycerin monostearate | 2.0 |
| Propylene glycol | 5.0 |
| Methyl 2-β-D-glucopyranosyloxy-5-hydroxybenzoate | 0.01 |
| Vitamin E (dl-α-tocopherol) | 0.05 |
| Perfume | q.s. |
| Sodium hydrogensulfite | 0.03 |
| Ethylparaben | 0.03 |
| Ion-exchanged water | Balance |

<Process>

Propylene glycol was added to and dissolved in ion-exchanged water and the mixture was heated and held at 70° C. (water phase). The other ingredients were melted with heat and held at 70° C. (oil phase). The oil phase was gradually added to the water phase for the purpose of preliminary emulsification, and thereafter, the mixture was uniformly emulsified by a homomixer. The emulsion was cooled to 30° C. under adequate stirring.

The cream obtained in Example 25 had a more excellent whitening effect than a cream which did not contain vitamin E.

EXAMPLE 26

(Cream)

| | |
|---|---|
| Solid paraffin | 5.0 |
| Beeswax | 10.0 |
| Vaseline | 15.0 |
| Liquid paraffin | 41.0 |
| Glycerin monostearate | 2.0 |
| Polyoxyethylene (20 mol) sorbitan monolaurate | 2.0 |
| Powder soap | 0.1 |
| Borax | 0.1 |
| 2-Pentyl 2-β-D-glucopyranosyloxy-5-hydroxybenzoate | 0.05 |
| 3-Methyl-1-butyl 2-β-D-glucopyranosyloxy-5-hydroxybenzoate | 0.05 |
| Perfume | q.s. |
| Sodium hydrogensulfite | 0.03 |
| Ethylparaben | 0.03 |
| Ion-exchanged water | Balance |

<Process>

Powder soap and borax were added to ion-exchanged water and the mixture was heated and held at 70° C. (water phase). The other ingredients were melted with heat and held at 70° C. (oil phase). The oil phase was gradually added to the water phase under stirring so as to induce reaction. After the end of the reaction, the reaction product was uniformly emulsified by a homomixer and thereafter the emulsion was cooled to 30° C. under adequate stirring.

The cream obtained in Example 26 had an excellent whitening effect and also an excellent chapped skin ameliorating effect.

EXAMPLE 27

(Milky Lotion)

| | |
|---|---|
| Stearic acid | 2.5 |
| Cetyl alcohol | 1.5 |
| Vaseline | 5.0 |
| Liquid paraffin | 10.0 |
| Polyoxyethylene (10 mol) monooleate | 2.0 |
| Polyethylene glycol 1500 | 3.0 |
| Triethanol amine | 1.0 |
| Dodecyl 2-β-D-glucopyranosyloxy-5-hydroxybenzoate | 0.001 |
| Sodium hydrogensulfite | 0.01 |
| Ethylparaben | 0.3 |
| Carboxyvinyl polymer (trade name: Carbopol 941, produced by B.F. Goodrich Chemical Company) | 0.05 |
| Perfume | q.s. |
| Ion-exchanged water | Balance |

<Process>

Carboxyvinyl polymer was dissolved in a small amount of ion-exchanged water (phase A). Polyethylene glycol 1500 and triethanol amine were added to the remaining ion-exchanged water, and the mixture was melted with heat and held at 70° C. (water phase). The other ingredients were melted with heat and held at 70° C. (oil phase). The oil phase was added to the water phase for the purpose of preliminary emulsification. Thereafter, the phase A was added, and the mixture was uniformly emulsified by a homomixer. The emulsion obtained was cooled to 30° C. under adequate stirring.

The milky lotion obtained in Example 27 had an excellent whitening effect and also an excellent chapped skin ameliorating effect.

EXAMPLE 28

(Milky Lotion Containing Ultraviolet Absorber)

(Oil phase portion)

| | |
|---|---|
| Stearyl alcohol | 1.5 |
| Squalane | 2.0 |
| Vaseline | 2.5 |
| Deodorized liquid lanolin | 1.5 |
| Evening primrose oil | 2.0 |
| Isopropyl myristate | 5.0 |
| Glycerin monooleate | 2.0 |
| Polyoxyethylene (60 mol) hardened castor oil | 2.0 |
| Tocopherol acetate | 0.05 |
| Ethylparaben | 0.2 |
| Butylparaben | 0.1 |
| 3-Methyl-3-pentyl 2-β-D-glucopyranosyloxy-5-hydroxybenzoate | 1.0 |
| Para-aminobenzoic acid | 0.1 |
| Perfume | q.s. |

(Water phase portion)

| | |
|---|---|
| Sodium hydrogensulfite | 0.001 |
| Glycerin | 5.0 |
| Sodium hyaluronate | 0.01 |
| Carboxyvinyl polymer (trade name: Carbopol 941, produced by B.F. Goodrich Chemical Company) | 0.02 |
| Potassium hydroxide | 0.2 |
| Ion-exchanged water | balance |

<Process>

The oil phase portion was dissolved at 70° C. The water phase portion was also dissolved at 70° C. The oil phase was mixed with the water phase, and after the mixture was emulsified by an emulsifier, it was cooled to 30° C. by a heat exchanger.

The milky lotion obtained in Example 28 had an excellent whitening effect and also an excellent chapped skin ameliorating effect.

EXAMPLE 29

(Milky Lotion)

| | |
|---|---|
| Microcrystalline wax | 1.0 |
| Beeswax | 2.0 |
| Lanolin | 20.0 |
| Liquid paraffin | 10.0 |
| Squalane | 5.0 |
| Sorbitan sesquioleate | 4.0 |
| Polyoxyethylene (20 mol) sorbitan monooleate | 1.0 |
| Propylene glycol | 7.0 |
| 2 6-Dimethyl-4-heptyl 2-β-D-glucopyranosyloxy-5-hydroxybenzoate | 3.0 |
| Ethylparaben | 0.3 |
| Sodium hydrogensulfite | 0.01 |
| Perfume | q.s. |
| Ion-exchanged water | Balance |

<Process>

Propylene glycol was added to the ion-exchanged water, and the mixture was heated to and held at 70° C. (water phase). The other ingredients were mixed, melted with heat and held at 70° C. (oil phase). The water phase was gradually added to the oil phase which was adequately stirred. The mixture was uniformly emulsified by a homo-mixer. The emulsion obtained was cooled to 30° C. under adequate stirring.

The milky lotion obtained in Example 29 had an excellent whitening effect and also an excellent chapped skin ameliorating effect.

EXAMPLE 30

(Jelly)

| | |
|---|---|
| 95% ethyl alcohol | 10.0 |
| Dipropylene glycol | 15.0 |
| Polyoxyethylene (50 mol) oleyl alcohol ether | 2.0 |
| Carboxyvinyl polymer (trade name: Carbopol 941, produced by B.F. Goodrich Chemical Company) | 1.0 |
| Caustic soda | 0.15 |
| L-arginine | 0.1 |
| Eicosyl 2-β-D-glucopyranosyloxy-5-hydroxybenzoate | 0.05 |
| Methylparaben | 0.2 |
| Ethylenediamine tetraacetate. trisodium. dihydrate | 0.05 |
| Perfume | q.s. |
| Ion-exchanged water | Balance |

<Process>

Carbopol 941 was uniformly dissolved in ion-exchanged water. Eicosyl 2-β-D-glucopyranosyloxy-3-hydroxybenzoate and polyoxyethylene (50 mol) oleyl alcohol ether were dissolved in 95% ethanol, and the aqueous Carbopol 941 solution was added to the solution. After the other ingredients were added to the mixed solution, the resultant solution was neutralized by caustic soda and L-arginine and thickened.

The jelly obtained in Example 30 had an excellent whitening effect.

EXAMPLE 31

(Toilet Lotion)

(Phase A)

| | |
|---|---|
| Ethanol (95%) | 10.0 |
| Polyoxyethylene (20 mol) octyldodecanol | 1.0 |
| Methylparaben | 0.15 |
| Pantothenyl ethyl ether | 0.1 |
| Hexyl 2-β-D-glucopyranosyloxy-5-hydroxybenzoate | 0.05 |

(Phase B)

| | |
|---|---|
| Potassium hydroxide | 0.1 |

(Phase C)

| | |
|---|---|
| Glycerin | 5.0 |
| Dipropylene glycol | 10.0 |
| Sodium hydrogensulfite | 0.03 |
| Carboxyvinyl polymer (trade name: Carbopol 941, produced by B.F. Goodrich Chemical Company) | 0.2 |
| Ion-exchanged water | Balance |

<Process>

The phase A and the phase C were uniformly dissolved respectively, and the phase A was added to the phase C so as to be solubilized. The phase B was then added to the mixed solution, and the resultant solution was packed.

The toilet lotion obtained in Example 31 had an excellent whitening effect and also a chapped skin ameliorating effect.

EXAMPLE 32

(Pack Containing Powder)

(Alcohol phase)

| | |
|---|---|
| 95% ethanol | 10.0 |
| Propylene glycol | 5.0 |
| 2-Hexadecyl 2-β-D-glucopyranosyloxy-5-hydroxybenzoate | 10.0 |
| Isopropyl 2-β-D-glucopyranosyl-5-hydroxysbenzoate | 1.0 |
| Perfume | q.s. |
| Coloring agent | q.s. |

(Water phase)

| | |
|---|---|
| Zinc white | 25.0 |
| Kaolin | 20.0 |
| Methylparaben | 0.3 |
| Glycerin | 5.0 |
| Ion-exchanged water | balance |

<Process>

After the water phase was uniformly prepared, the alcohol phase prepared at room temperature was added thereto and the mixture was uniformly mixed.

The pack obtained in Example 32 had an excellent whitening effect and also an excellent chapped skin ameliorating effect.

EXAMPLE 33

(Cream)

| | |
|---|---|
| Solid paraffin | 5.0 |
| Beeswax | 10.0 |
| Vaseline | 15.0 |
| Liquid paraffin | 41.0 |
| Glycerin monostearate | 2.0 |
| Polyoxyethylene (20 mol) sorbitan monolaurate | 2.0 |
| Powder soap | 0.1 |
| Borax | 0.2 |
| Benzyl 2-β-D-glucopyranosyloxy-5-hydroxybenzoate | 0.05 |
| Sodium hydrogensulfite | 0.03 |
| Ethylparaben | 0.3 |
| Perfume | q.s. |
| Ion-exchanged water | Balance |

<Process>

Powder soap and borax were added to ion-exchanged water and the mixture was heated and held at 70° C. (water phase). The other ingredients were melted with heat and held at 70° C. (oil phase). The oil phase was gradually added to the water phase under stirring so as to induce reaction. After the end of the reaction, the reaction product was uniformly emulsified by a homomixer and thereafter the emulsion was cooled to 30° C. under adequate stirring.

The cream obtained in Example 33 had an excellent whitening effect and also an excellent chapped skin ameliorating effect.

As explained above, since a glycoside of hydroxysalicylic acid and/or a glycoside of a hydroxysalicylate according to the present invention has a more excellent whitening effect than a conventional compound prepared for the same purpose, it can produce the desired effect even with a small amount. In addition, the compound of the present invention is safe. A glycoside of gentisate according to the present invention also has a chapped skin ameliorating effect. Accordingly, it is possible to produce a highly safe external preparation for skin having an excellent whitening effect and/or an excellent chapped skin ameliorating effect by mixing this compound.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An external preparation for skin comprising at least one of the glycosides of hydroxysalicylic acid and/or the glycosides of esters of hydroxysalicylic acid represented by the following formula 1;

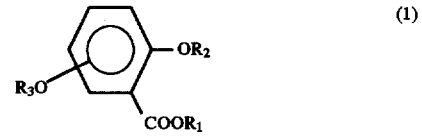

(1)

wherein $R_1$ represents one selected from the group consisting of a saturated hydrocarbon group and an unsaturated hydrocarbon group which have 1 to 20 carbon atoms and which may be of either a straight-chain or a branched-chain, and one of $R_2$ and $R_3$ represents a monosaccharide residue and the other hydrogen.

2. An external preparation for the skin comprising at least one of the glycosides of hydroxysalicylic acid and/or the glycosides of esters of hydroxysalicylic acid represented by the following formula 2:

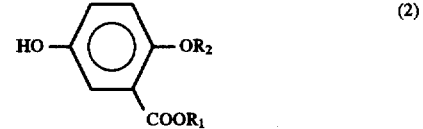

(2)

wherein $R_1$ represents one selected from the group consisting of a saturated hydrocarbon group and an unsaturated hydrocarbon group which have 1 to 20 carbon atoms and which may be either a straight-chain or a branched-chain, and $R_2$ represents one selected from the group consisting of pentose residue, hexose residue, amino sugar residue and urocanic acid residue.

3. An external preparation for the skin according to claim 1, wherein said $R_2$ represents a glucopyranosyl residue.

* * * * *